(12) United States Patent
Dean

(10) Patent No.: US 7,604,798 B2
(45) Date of Patent: Oct. 20, 2009

(54) METHODS AND COMPOSITIONS FOR IMPORTING NUCLEIC ACIDS INTO CELL NUCLEI

(75) Inventor: David A. Dean, Oak Park, IL (US)

(73) Assignee: Northwestern University, Evanston, IL (US)

(*) Notice: Subject to any disclaimer, the term of this patent is extended or adjusted under 35 U.S.C. 154(b) by 0 days.

(21) Appl. No.: 11/182,933

(22) Filed: Jul. 15, 2005

(65) Prior Publication Data

US 2006/0070133 A1 Mar. 30, 2006

Related U.S. Application Data

(60) Provisional application No. 60/588,206, filed on Jul. 15, 2004.

(51) Int. Cl.
*A01N 63/00* (2006.01)
*C07H 21/02* (2006.01)
*C07H 21/04* (2006.01)
*C12Q 1/70* (2006.01)

(52) U.S. Cl. ..................... 424/93.21; 536/23.1; 435/5

(58) Field of Classification Search ..................... None
See application file for complete search history.

(56) References Cited

U.S. PATENT DOCUMENTS

| | | | |
|---|---|---|---|
| 4,650,764 | A | 3/1987 | Temin et al. |
| 4,797,368 | A | 1/1989 | Carter et al. |
| 4,861,719 | A | 8/1989 | Miller |
| 4,980,289 | A | 12/1990 | Temin et al. |
| 5,124,263 | A | 6/1992 | Temin et al. |
| 5,139,941 | A | 8/1992 | Muzyczka et al. |
| 5,399,346 | A | 3/1995 | Anderson et al. |
| 5,459,127 | A | 10/1995 | Felgner et al. |
| 5,580,859 | A | 12/1996 | Felgner et al. |
| 5,589,466 | A | 12/1996 | Felgner et al. |

FOREIGN PATENT DOCUMENTS

| | | |
|---|---|---|
| EP | 453 242 | 4/1991 |
| EP | 178 220 | 1/1992 |
| WO | WO 89/07150 | 8/1989 |
| WO | WO 90/02806 | 3/1990 |
| WO | WO 91/18088 | 11/1991 |
| WO | WO 92/05263 | 4/1992 |
| WO | WO 93/09239 | 5/1993 |
| WO | WO 94/12649 | 6/1994 |
| WO | WO 94/21807 | 9/1994 |
| WO | WO 94/26914 | 11/1994 |
| WO | WO 94/28152 | 12/1994 |
| WO | WO 94/28938 | 12/1994 |
| WO | WO 95/02697 | 1/1995 |
| WO | WO 95/07358 | 3/1995 |
| WO | WO 95/18863 | 7/1995 |
| WO | WO 95/21931 | 8/1995 |
| WO | WO 96/17823 | 6/1996 |
| WO | WO 96/17823 | 7/1996 |
| WO | WO 96/22378 | 7/1996 |
| WO | WO 96/25508 | 8/1996 |
| WO | WO 97/34915 | 9/1997 |

OTHER PUBLICATIONS

Cowan et al., 2003, Xenotransplantation, 10: 223-231.*
Glasser et al., 2000, Am. J. Physiol. Lung Cell Mol. Physiol., 278: L933-L945.*
Xu et al., 2000, Circulation Research, 87: 254-260.*
Glasser et al., 1990, JBC, 265: 21986-21991.*
SuperFect Transfection Reagent Handbook [online], 2002 [retrieved Apr. 10, 2008]. Retrieved from the Internet:<http://www1.qiagen.com/HB/SuperFectTransfectionReagent_EN, pp. 1-31.*
Dowty et al., "Plasmid DNA Entry Into Postmitotic Nuclei of Primary Rat Myotubes," PNAS 92:4572 (1995).
Samulski et al., "A recombinant plasmid from which an infectious adeno-associated virus genome can be excised in vitro and its use to study viral replication," J. Virol., 61:3096-3101 [1987].
Samulski et al., "Helper-free stocks of recombinant adeno-associated viruses: normal integration does not require viral gene expression," J. Virol., 63:3822-3828 [1989].
Markowitz et al., "A safe packaging line for gene transfer: separating viral genes on two different plasmids," J. Virol., 62:1120 [1988].
Kuo et al., "Efficient gene transfer into primary murine lymphocytes obviating the need for drug selection," Blood 82:845 [1993].
Bender et al., "Evidence that the packaging signal of Moloney murine leukemia virus extends into the gag region," J. Virol., 61:1639 [1987].
Felgner et. al., Lipofection: A Highly Efficient, Lipid-Mediated DNA-Transfection Procedure, Proc. Natl. Acad. Sci. USA 84:7413-7417 [1987].
Machey, et al., "Gene Transfer from Targeted Liposomes to Specific Lymphoid Cells by Electroporation," Proc. Natl. Acad. Sci. USA 85:8027-8031 [1988].
Wilson et al., "Hepatocyte-directed gene transfer in vivo leads to transient improvement of hypercholesterolemia in low density lipoprotein receptor- deficient rabbits," J. Biol. Chem., 267:963-967 [1992].
Wu and Wu, "Receptor-mediated gene delivery and expression in vivo ," J. Biol. Chem., 263:14621-14624 [1988].
Williams et al., "Introduction of Foreign Genes into Tissues of Living Mice by DNA-Coated Microprojectiles," Proc. Natl. Acad. Sci. USA 88:2726-2730 [1991].
Wu and Wu, "Receptor-mediated in vitro gene transformation by a soluble DNA carrier system [published erratum appears in J Biol Chem Jan. 5, 1988;263(1):588," J. Biol. Chem., 262:4429-4432 [1987].
Dean, "Import of plasmid DNA into the nucleus is sequence specific," Exp. Cell. Res. 230:293 (1997).

(Continued)

*Primary Examiner*—Joanne Hama
(74) *Attorney, Agent, or Firm*—Casimir Jones SC

(57) ABSTRACT

The present invention relates to methods and compositions for importing DNA into the nuclei of a specific cell type. In particular, the present invention provides methods and compositions for specifically targeting the nuclei of pulmonary cells.

5 Claims, 6 Drawing Sheets

OTHER PUBLICATIONS

Miller and Rosman, "Improved REtroviral Vectors for Gene Transfer and Expression," Biotechniques, 7:980-990 [1992].

Kaplitt et al., "Expression of a Functional Foreign Gene in Adult Mammalian Brain following in Vivo Transfer via a Herpes Simplex Virus Type 1 Defective Viral Vector," Mol. Cell. Neurosci., 2:320-330 [1991].

Stratford-Perricaudet et al., Widespread long-term gene transfer to mouse skeletal muscles and heart, J. Clin. Invest., 90:626-630 [1992].

La Salle et al., "An Adenovirus Vector For Gene Transfer into Neurons and Glia in the Brain," Science 259:988-990 [1993].

Lebkowski et al., "Adeno-associated virus: a vector system for efficient introduction and integration of DNA into a variety of mammalian cell types," Mol. Cell. Biol., 8:3988-3996 [1988].

Mav1, "Transcription Mapping of Mouse Adenovirus Type 1 Early REgion 3," Beard et al., Virol., 75-81 [1990].

Levrero et al., "Defective and nondefective adenovirus vectors for expressing foreign genes in vitro and in vivo," Gene 101:195 [1991].

Graham, "Covalently closed circles of human adenovirus DNA are infectious," EMBO J., 3:2917 [1984].

Mann et al., "Construction of a retrovirus packaging mutant and its use to produce helper-free defective retrovirus," Cell 33:153 [1983].

McCormick, "Human Gene Therapy: The First Round," BioTechnol., 3:689 [1985].

Bernstein et al. "Gene Transfer with Retrovirus Vectors," Genet. Eng., 7:235 [1985].

Felgner and Ringold, "Cationic liposome-mediated transfection," Nature 337:387-388 [1989].

Curiel et al., "High-efficiency gene transfer mediated by adenovirus coupled to DNA-polylysine complexes," Hum. Gene Ther., 3:147-154 [1992].

Dean et al., "Sequence requirements for plasmid nuclear import," Exp Cell Res., 253(2):713-22 (1999).

Vacik et al., "Cell-specific nuclear import of plasmid DNA," Gene Ther., 6(6):1006-14 (1999).

Glasser et al., "Human SP-C gene sequences that confer lung epithelium-specific expression in transgenic mice," Am J Physiol Lung CellMol Physiol., 278(5):L933-45 (2000).

Munkonge et al., "Emerging significance of plasmid DNA nuclear import in gene therapy," Adv Drug Deliv Rev., 55(6):749-60 (2003).

Young et al., "Effect of a DNA nuclear targeting sequence on gene transfer and expression of plasmids in the intact vasculature," Gene Ther., 10(17):1465-70 (2003).

Glasser et al., "Structure and expression of the pulmonary surfactant protein SP-C gene in the mouse ," J Biol Chem., 265(35):21986-91 (1990).

Glasser et al., "Genetic element from human surfactant protein SP-C gene confers bronchiolar-alveolar cell specificity in transgenic mice," Am J Physiol., 261(4 Pt. 1):L349-56 (1991).

Kelly et al., "Transcription of the Lung-specific Surfactant Protein C Gene Is Mediated by Thyroid Transcription Factor 1," J Biol Chem., 271(12):6881-8 (1996).

Korfhagen et al., "Cis-Acting Sequences from a Human Surfactant Protein Gene Confer Pulmonary-Specific Gene Expression in Transgenic Mice," PNAS, 87(16):6122-6 (1990).

Bachurski et al., "Nuclear factor I/thyroid transcription factor 1 interactions modulate surfactant protein C transcription," Mol Cell Biol., 23(24):9014-24 (2003).

Bachurski et al., "Nuclear factor I family members regulate the transcription of surfactant protein-C," Mol Cell Biol., 272(52):32759-66 (1997).

Liu et al., "GATA-6 and Thyroid Transcription Factor-1 Directly Interact and Regulate Surfactant Protein-C Gene Expression," J Biol Chem., 277(6):4519-25 (2002).

Wilson et al., "Nuclear Import of Plasmid DNA in Digitonin-permeabilized Cells Requires Both Cytoplasmic Factors and Specific DNA Sequences ," J Biol Chem., 274(31):22025-32 (1999).

Adam et al., "In Vitro Nuclear Protein Import Using Permeabilized Mammalian Cells," Methods Cell Biol., 35:469-82 (1991).

Park et al., "TAZ Interacts with TTF-1 and Regulates Expression of Surfactant Protein-C ," J Biol Chem., 279(17):17384-90 (2004).

DeWitt et al., ""Diversomers": An Approach to Nonpeptide, Nonoligomeric Chemical Diversity,"PNAS, 90:6909-6913 (1993).

Ulmer et al., "Heterologous protection against influenza by injection of DNA encoding a viral protein," Science 259:1745-1748 [1993].

DeGiulio et al., "The Human Surfactant Protein C (SP-C) Promoter Mediates Plasmid Nuclear Import Specifically in Vlveolar Epithelial Cells," American Thoracic Society Annual Meeting in San Diego, May 21-25, 2005.

DeGiulio et al., "Alveolar Epithelial Cell-Specific Plasmid Nuclear Import," American Thoracic Society Annual Meeting in St. Louis, Jun. 1 to 5, 2005.

* cited by examiner

Figure 1
SEQ ID NO:1

5'-GGCAGCAGGGGCAGGTGCCAGCAAGGAAGGCAGGCACGCCAGGAAGACA
CCCATGGTGAGAAGTGCAGATGGCCCGAGGGCAAGTTTGCTCAACTCACCCA
GGTTTGCTCTTGCTGGGGCCAAGAGGACTCATGTGCCAGGGCCAAGGGCCCT
TGGGGGCTCTCACAGGGGGCTTATCTGGGCTTCGGTTCTGGAGGGCCAGGAA
CAAACAGGCTTCAAAGCCAAGGGCTTGGCTGGCACACAGGGGGCTTGGTCCT
TCACCTCTGTCCCCTCTCCCTACGGACACATATAAGACCCTGGTCACACCTGG
GAGAGGAGgagaggagagcatagcacctgcagcaagatggatgtgggcagcaaag-3'

METHODS AND COMPOSITIONS FOR IMPORTING NUCLEIC ACIDS INTO CELL NUCLEI

This application claims priority to U.S. provisional application No. 60/588,206 filed Jul. 15, 2004, which is hereby incorporated herein by reference in its entirety.

This invention was made in part during work partially supported by grant PO1 HL71643 from the National Institute of Health. The government may have certain rights in the invention.

FIELD OF THE INVENTION

The present invention relates to methods and compositions for importing DNA into the nuclei of a specific cell type. In particular, the present invention provides methods and compositions for specifically targeting the nuclei of pulmonary cells.

BACKGROUND OF THE INVENTION

Despite the promise and excitement of gene therapy, it is still a long way from practice. Two major problems hindering gene therapy are that (1) gene transfers to non-dividing cells are still extremely inefficient, and (2) gene transfer to specific desired non-dividing cells within a population of other cell types is even more inefficient. Thus, any way to increase the amount of gene transfer will greatly benefit this emerging field.

Many techniques and vectors for gene therapy have been developed to target genes to cells, including replication-deficient recombinant retroviruses, adenoviruses, and adeno-associated viruses, as well as non-viral vectors such as ligand-DNA conjugates or DNA lipofection. However, most targeting techniques developed to date have only addressed the ability to internalize the DNA into the cytoplasm of the cell. It is clear that gene therapy relies on the ability of targeted genes to enter the nucleus. This is true regardless of how the DNA or RNA is targeted to the cell; once within the cytoplasm, the gene must become nuclear to be transcribed, replicated, and maintained either in an integrated or episomal state, yet there has been little attention directed toward either discovering or exploiting the mechanisms used by the cell to direct DNA to the nucleus.

The promise and potential of gene therapy techniques to cure or to alleviate symptoms in a multitude of disorders and diseases results in a continuing need for ways to increase the amount of gene transfer to cells. Ideally, a way to increase the amount of gene transfer to the nucleus of a specific cell type would exist for cell-specific targeting of gene therapy.

SUMMARY OF THE INVENTION

The present invention relates to methods and compositions for importing DNA into the nuclei of a specific cell type. In particular, the present invention provides methods and compositions for specifically targeting the nuclei of pulmonary epithelial cells.

Accordingly, in some embodiments, the present invention provides a composition comprising a cell specific nuclear targeting signal operably linked to a nucleic acid of interest, wherein the cell specific nuclear targeting signal comprises at least a portion of a surfactant protein C promoter region. In some embodiments, at least a portion of a surfactant protein C promoter region is SEQ ID NO: 1. In some embodiments, the cell specific nuclear targeting signal is configured to direct the expression of the nucleic acid of interest in a pulmonary epithelial cell. In some embodiments, the nucleic acid of interest is a gene. In further embodiments, the nucleic acid of interest is a heterologous gene. In other embodiments, the nucleic acid of interest encodes an antisense RNA. In still further embodiments, the nucleic acid of interest encodes a siRNA or mRNA.

The present invention further provides a vector comprising the composition. In some embodiments, the vector is a plasmid or a viral vector (e.g., a retroviral vector, an adenoviral vector, an adeno associated viral vector, or a lentiviral vector). The present invention additionally provides a host cell comprising the vector. In some embodiments, the host cell is in vitro. In other embodiments, the host cell is in vivo. In some embodiments, the host cell is in a non-human mammal. In other embodiments, the host cell is in a human. In certain preferred embodiments, the host cell is a pulmonary epithelial cell. In other embodiments, the host cell is a non-dividing cell.

In yet other embodiments, the present invention provides a method for tissue specific nuclear import, comprising: providing a construct comprising cell specific nuclear targeting signal operably linked to a nucleic acid of interest, wherein the cell specific nuclear targeting signal comprises at least a portion of a surfactant protein C promoter region; and a cell; and contacting the cell with the construct under conditions such that the nucleic acid of interest is expressed in the nucleus of the cell. In some embodiments, the at least a portion of a surfactant protein C promoter region is SEQ ID NO: 1. In some embodiments, the nucleic acid of interest is a gene. In other embodiments, the nucleic acid of interest encodes an antisense RNA. In yet other embodiments, the nucleic acid of interest encodes a siRNA or mRNA. In some embodiments, the construct is within a vector. In some embodiments, the vector is a plasmid or a viral vector (e.g., a retroviral vector, an adenoviral vector, an adeno associated viral vector, or a lentiviral vector). In some embodiments, the cell is in vitro. In other embodiments, the cell is in vivo. In some embodiments, the cell is in a non-human mammal. In certain preferred embodiments, the cell is a pulmonary epithelial cell. In some embodiments, the cell is a non-dividing cell. In some embodiments, the method further comprises the step of contacting the cell with a test compound. In some embodiments, the test compound alters the phenotype of the cell. In other embodiments, the method further comprises the step of delivering said construct to said cell through the trachea. In further embodiments, the method further comprises the step of administering in vivo electroporation to said cell.

DESCRIPTION OF THE DRAWING

FIG. 1 shows the nucleic acid sequence of the human SP-C promoter (SEQ ID NO:1).

FIG. 5A shows no nuclear import. FIG. 5B shows intermediate nuclear import. FIG. 5C shows total nuclear import.

FIG. 6A shows naïve lung stained with antibodies against luciferase. FIG. 6B shows expression of luciferase in all pulmonary cell types following endotracheal delivery of pCMV-Lux-DTS with the SV40 enhancer. FIG. 6C shows expression of luciferase confined to smooth muscle cells after endotracheal delivery of pSMGA-Lux without the SV40 enhancer. FIG. 6D shows immunohistochemical staining of the smooth muscle marker alpha actin.

DEFINITIONS

Figure 2:
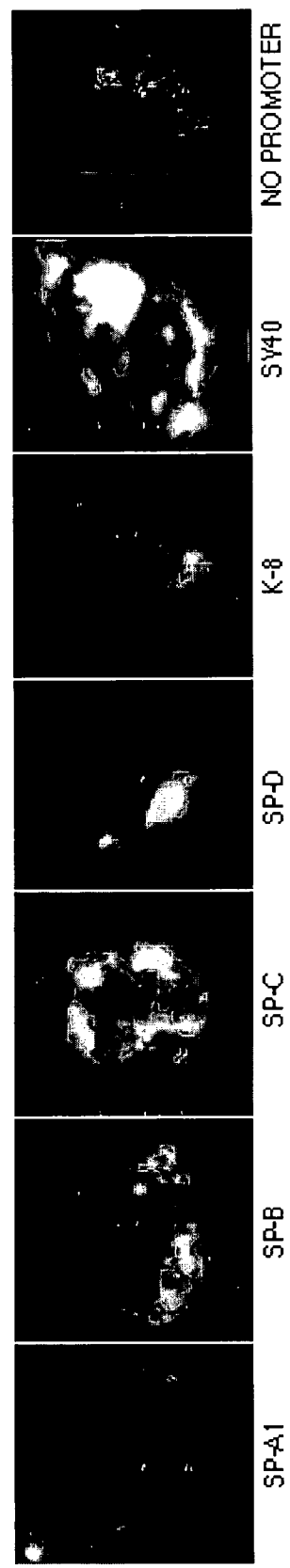
FIG. 2 depicts A549 cells that have been cytoplasmically injected with plasmids containing the indicated promoters, showing that the human SP-C promoter mediates DNA nuclear import in alveolar epithelial cells.

As used herein, the term "nuclear targeting signal" refers to a nucleic acid sequence, that, when operably linked to a nucleic acid sequence of interest, directs import of the nucleic acid into the nucleus of cell. In certain embodiments, the nuclear targeting signal further directs the expression of the nucleic acid of interest in the nucleus. In particularly preferred embodiments, the nuclear targeting signal is "cell specific."

As used herein, "cell-specific" means the targeting of DNA to the nuclei of a specific cell type or types of interest only, and not to the nuclei of other cell types. The "specific cell type" refers to a "type" of cell (for example, pulmonary epithelial cells). In further embodiments, "substantially cell-specific" means the preferential targeting of DNA to the nuclei of a specific cell type or types more so than to the nuclei of other cells types. In some preferred embodiments, the SP-C promoter sequence shown in SEQ ID NO:1 is used as a cell specific nuclear targeting signal.

As used herein, "nuclear DNA binding proteins" refer to DNA binding proteins that reside in the nucleus. These nuclear DNA binding proteins are characterized in that they bind to short DNA sequences with sequence specificity, and they are transported to the nucleus of a cell because they contain a nuclear localization signal (NLS) or because they complex with one or more other proteins that contain an NLS. Nuclear DNA binding proteins have different functions in the regulation of DNA transcription and/or replication. Nuclear DNA binding proteins include, for example, eukaryotic transcription factors, DNA replication factors, and telomere or centromere binding proteins. For a general discussion of nuclear, DNA binding proteins, see e.g., Nigg (Nature 386: 779 (1997)). Preferably, the nuclear DNA binding protein is a transcription factor.

As used herein, "transcription factors" refer to proteins that promote RNA polymerase recognition and/or initiation and/or activation and/or repression of promoters (DNA sequences). The binding of RNA polymerase to a promoter is important to initiate transcription, which is the process by which the information contained in the DNA is copied into a single-stranded RNA molecule by RNA polymerase. The genetic information present in a mRNA molecule is then translated into a protein.

The term "gene" refers to a nucleic acid (e.g., DNA or RNA) sequence that comprises coding sequences necessary for the production of a polypeptide or precursor (e.g., a protein of interest). The polypeptide can be encoded by a full length coding sequence or by any portion of the coding sequence so long as the desired activity or functional properties (e.g., enzymatic activity, ligand binding, signal transduction, etc.) of the full-length or fragment are retained. The term also encompasses the coding region of a structural gene and the including sequences located adjacent to the coding region on both the 5' and 3' ends for a distance of about 1 kb on either end such that the gene corresponds to the length of the full-length mRNA. The sequences that are located 5' of the coding region and which are present on the mRNA are referred to as 5' untranslated sequences. The sequences that are located 3' or downstream of the coding region and that are present on the mRNA are referred to as 3' untranslated sequences. The term "gene" encompasses both cDNA and genomic forms of a gene. A genomic form or clone of a gene contains the coding region interrupted with non-coding sequences termed "introns" or "intervening regions" or "intervening sequences." Introns are segments of a gene that are transcribed into nuclear RNA (hnRNA); introns may contain regulatory elements such as enhancers. Introns are removed or "spliced out" from the nuclear or primary transcript; introns therefore are absent in the messenger RNA (mRNA) transcript. The mRNA functions during translation to specify the sequence or order of amino acids in a nascent polypeptide.

As used herein, the term "heterologous gene" refers to a gene that is not in its natural environment. For example, a heterologous gene includes a gene from one species introduced into another species. A heterologous gene also includes a gene native to an organism that has been altered in some way (e.g., mutated, added in multiple copies, linked to non-native regulatory sequences, etc). Heterologous genes are distinguished from endogenous genes in that the heterologous gene sequences are typically joined to DNA sequences that are not found naturally associated with the gene sequences in the chromosome or are associated with portions of the chromosome not found in nature (e.g., genes expressed in loci where the gene is not normally expressed).

Where "amino acid sequence" is recited herein to refer to an amino acid sequence of a naturally occurring protein molecule, "amino acid sequence" and like terms, such as "polypeptide" or "protein" are not meant to limit the amino acid sequence to the complete, native amino acid sequence associated with the recited protein molecule.

In addition to containing introns, genomic forms of a gene may also include sequences located on both the 5' and 3' end of the sequences that are present on the RNA transcript. These sequences are referred to as "flanking" sequences or regions (these flanking sequences are located 5' or 3' to the non-translated sequences present on the mRNA transcript). The 5' flanking region may contain regulatory sequences such as promoters and enhancers that control or influence the transcription of the gene. The 3' flanking region may contain sequences that direct the termination of transcription, post-transcriptional cleavage and polyadenylation.

The term "wild-type" refers to a gene or gene product that has the characteristics of that gene or gene product when isolated from a naturally occurring source. A wild-type gene is that which is most frequently observed in a population and is thus arbitrarily designed the "normal" or "wild-type" form of the gene. In contrast, the terms "modified", "mutant", and "variant" refer to a gene or gene product that displays modifications in sequence and or functional properties (i.e., altered characteristics) when compared to the wild-type gene or gene product. It is noted that naturally-occurring mutants can be isolated; these are identified by the fact that they have altered characteristics when compared to the wild-type gene or gene product.

A gene may produce multiple RNA species that are generated by differential splicing of the primary RNA transcript. cDNAs that are splice variants of the same gene will contain regions of sequence identity or complete homology (representing the presence of the same exon or portion of the same exon on both cDNAs) and regions of complete non-identity (for example, representing the presence of exon "A" on cDNA 1 wherein cDNA 2 contains exon "B" instead). Because the two cDNAs contain regions of sequence identity they will both hybridize to a probe derived from the entire gene or portions of the gene containing sequences found on both cDNAs; the two splice variants are therefore substantially homologous to such a probe and to each other.

The term "fragment" as used herein refers to a polypeptide that has an amino-terminal and/or carboxy-terminal deletion as compared to the native protein, but where the remaining amino acid sequence is identical to the corresponding positions in the amino acid sequence deduced from a full-length cDNA sequence. Fragments typically are at least 4 amino acids long, preferably at least 20 amino acids long, usually at least 50 amino acids long or longer, and span the portion of the polypeptide required for intermolecular binding of the compositions (claimed in the present invention) with its various ligands and/or substrates.

The term "naturally-occurring" as used herein as applied to an object refers to the fact that an object can be found in nature. For example, a polypeptide or polynucleotide sequence that is present in an organism (including viruses) that can be isolated from a source in nature and which has not been intentionally modified by man in the laboratory is naturally-occurring.

The term "antigenic determinant" as used herein refers to that portion of an antigen that makes contact with a particular antibody (i.e., an epitope). When a protein or fragment of a protein is used to immunize a host animal, numerous regions of the protein may induce the production of antibodies that bind specifically to a given region or three-dimensional structure on the protein; these regions or structures are referred to as antigenic determinants. An antigenic determinant may compete with the intact antigen (i.e., the "immunogen" used to elicit the immune response) for binding to an antibody.

The term "transfection" as used herein refers to the introduction of foreign DNA into eukaryotic cells. Transfection may be accomplished by a variety of means known to the art including calcium phosphate-DNA co-precipitation, DEAE-dextran-mediated transfection, polybrene-mediated transfection, electroporation, microinjection, liposome fusion, lipofection, protoplast fusion, retroviral infection, and biolistics.

The term "stable transfection" or "stably transfected" refers to the introduction and integration of foreign DNA into the genome of the transfected cell. The term "stable transfectant" refers to a cell that has stably integrated foreign DNA into the genomic DNA.

The term "transient transfection" or "transiently transfected" refers to the introduction of foreign DNA into a cell where the foreign DNA fails to integrate into the genome of the transfected cell. During the time the foreign DNA persists in the nucleus it is subject to the regulatory controls that govern the expression of endogenous genes in the chromosomes. The term "transient transfectant" refers to cells that have taken up foreign DNA but have failed to integrate this DNA.

The term "calcium phosphate co-precipitation" refers to a technique for the introduction of nucleic acids into a cell. The uptake of nucleic acids by cells is enhanced when the nucleic acid is presented as a calcium phosphate-nucleic acid co-precipitate. The original technique of Graham and van der Eb (Graham and van der Eb, Virol., 52:456 [1973]), has been modified by several groups to optimize conditions for particular types of cells. The art is well aware of these numerous modifications.

The term "test compound" refers to any chemical entity, pharmaceutical, drug, and the like that can be used to treat or prevent a disease, illness, sickness, or disorder of bodily function, or otherwise alter the physiological or cellular status of a sample. Test compounds comprise both known and potential therapeutic compounds. A test compound can be determined to be therapeutic by screening using the screening methods of the present invention. A "known therapeutic compound" refers to a therapeutic compound that has been shown (e.g., through animal trials or prior experience with administration to humans) to be effective in such treatment or prevention.

As used herein, the term "response," when used in reference to an assay, refers to the generation of a detectable signal (e.g., accumulation of reporter protein, increase in ion concentration, accumulation of a detectable chemical product).

As used herein, the term "membrane protein" refers to a protein that spans the lipid by-layer membrane or a cell or organelle.

As used herein, the term "ion channel protein" refers to proteins that control the ingress or egress of ions across cell membranes. Examples of ion channel proteins include, but are not limited to, the $Na^+$—$K^+$ ATPase pump, the $Ca^{2+}$ pump, and the $K^+$ leak channel.

As used herein, the term "purified" refers to molecules, either nucleic or amino acid sequences, that are removed from their natural environment, isolated or separated. An "isolated nucleic acid sequence" is therefore a purified nucleic acid sequence. "Substantially purified" molecules are at least 60% free, preferably at least 75% free, and more preferably at least 90% free from other components with which they are naturally associated.

As used herein, the term "siRNAs" refers to small interfering RNAs. In some embodiments, siRNAs comprise a duplex, or double-stranded region, of about 18-25 nucleotides long; often siRNAs contain from about two to four unpaired nucleotides at the 3' end of each strand. At least one strand of the duplex or double-stranded region of a siRNA is substantially homologous to, or substantially complementary to, a target RNA molecule. The strand complementary to a target RNA molecule is the "antisense strand;" the strand homologous to the target RNA molecule is the "sense strand," and is also complementary to the siRNA antisense strand. siRNAs may also contain additional sequences; non-limiting examples of such sequences include linking sequences, or loops, as well as stem and other folded structures. siRNAs appear to function as key intermediaries in triggering RNA interference in invertebrates and in vertebrates, and in triggering sequence-specific RNA degradation during posttranscriptional gene silencing in plants.

The term "RNA interference" or "RNAi" refers to the silencing or decreasing of gene expression by siRNAs. It is the process of sequence-specific, post-transcriptional gene silencing in animals and plants, initiated by siRNA that is homologous in its duplex region to the sequence of the silenced gene. The gene may be endogenous or exogenous to the organism, present integrated into a chromosome or present in a transfection vector that is not integrated into the genome. The expression of the gene is either completely or partially inhibited. RNAi may also be considered to inhibit the function of a target RNA; the function of the target RNA may be complete or partial.

DETAILED DESCRIPTION OF THE INVENTION

The present invention relates to methods and compositions for importing DNA into the nuclei of a specific cell type. In particular, the present invention provides methods and compositions for specifically targeting the nuclei of pulmonary epithelial cells.

In many targets of gene therapy and biomedical research, it is desirable to transfer genes only to one cell type within a tissue. Three different approaches are available for such cell-specific gene expression. First, the delivery of genes to certain cell types based on the site and physical method of delivery. In other words, by injecting DNA into the big toe, gene transfer will be mainly to the big toe, not the eye. The second approach is to employ cell-specific promoters to drive gene expression only in desired cell types. In this case, DNA is delivered to all cells within the tissue (or as many as the delivery method allows), and gene expression is limited to those cells in which the promoter is functional. The methods of the present invention utilize a third way, which is to limit gene expression to certain cell types by limiting nuclear import of the DNA to certain cell types.

The nuclear envelope is one of the major barriers to gene transfer. In non-dividing cells, the nucleus is surrounded by a double-membraned envelope that is impermeable to large molecules lacking discreet signals for nuclear import. Nuclear import of plasmids in non-dividing cells is sequence-specific. Plasmids containing a DNA nuclear import sequences are able to enter the nucleus, while those lacking such a sequence remain in the cytoplasm until cell division, or until they are degraded. The common feature to these import sequences is that they contain binding sites for transcription factors, that in turn harbor protein signals (nuclear localization signals, NLS) that interact with the cell's machinery for nuclear protein import. Thus, the DNA becomes coated with protein NLSs and is able to enter the nucleus.

Using transformed cell lines and primary cultured cells, it has been shown that plasmid DNA is able to enter the nuclei of cells in the absence of cell division and its accompanying nuclear envelope breakdown (Dean, Exp. Cell. Res. 230:293 (1997)). As with all other macromolecular exchange between the cytoplasm and nucleus (for a review, see Nigg, 1997, supra), DNA nuclear entry appears to be mediated by the nuclear pore complex (Dean, 1997, supra; Dowty et al., PNAS 92:4572 (1995)). A 366 bp sequence of DNA containing the simian virus 40 (SV40) origin of replication and early promoter has been identified that is absolutely necessary for the nuclear entry of plasmid DNA in cultured cell lines derived from monkey, rat, mouse, hamster, and human origin, as well as non-transformed primary cells from rat, chicken, and human tissues (Dean 1997, supra). Thus, nuclear import of plasmid DNA is signal-dependent and occurs in all eukaryotic cells tested to date. This DNA nuclear localization signal has been further localized to regions within the 366 bp DNA fragment (see also PCT International Publication No. WO 97/34915, published Sep. 25, 1997, by Dean (the contents of which are hereby incorporated by reference)). These results demonstrate that transport of DNA into the nucleus is sequence-specific.

Experiments conducted during the course of development of the present invention demonstrated that a DNA sequence from the human surfactant protein C (SP-C) promoter drives pulmonary epithelial cell-specific DNA nuclear import. This is an improvement over current methods because it can be used in addition to these other methods to greatly increase the likelihood of cell-specific gene transfer and safety.

This sequence can be incorporated into any gene-expressing vector to direct gene expression of the vector to pulmonary epithelial cells alone, based on restricted nuclear import. Such compositions and methods find use in a variety of applications including, but not limited to, gene therapy approaches to treat any number of pulmonary diseases and disorders, including cystic fibrosis, acute lung injury, acute respiratory distress syndrome, pulmonary fibrosis, and asthma, drug screening (e.g., in cell culture) and other research applications. Drug screening and research applications are also provided by the present invention. In some embodiments, expression of the vector within the targeted cell is detected by changes in cell function. In further embodiments, changes in cell function after expression of a vector indicate the level of activity of a test compound.

Many examples of DNA molecules for which it would be desirable to import the molecules into a specific cell type should be readily apparent to those skilled in the art. For example, many proposed gene therapy techniques would benefit from the ability to import a DNA molecule into the nucleus according to the subject invention. Numerous examples of DNA molecules that could be imported are known. For example, Knowles et al. (N Engl. J. Med. 333:823 (1995)) disclose that the expression of the cystic fibrosis transmembrane conductance regulator in pulmonary epithelia is useful in the treatment and/or prevention of cystic fibrosis lung disease.

In other embodiments, the DNA molecule to be targeted expresses an RNA that does not code for a protein. For example, an antisense oligonucleotide or an siRNA that inhibits the translation or stability of a cellular mRNA, or a stable RNA such as a tRNA, a rRNA, a UsnRNA (involved in mRNA splicing), or 7SL RNA which is part of the signal recognition particle (SRP) for protein translocation into the endoplasmic reticulum. In yet other embodiments, the nucleic acid of interest encodes a ribozymes, an RNAs that repair mutant mRNAs (Sullenger and Cech Nature 371:619 (1994)).

I. Vectors

In preferred embodiments, the nuclear targeting constructs of the present invention are contained within a vector. In some embodiments, the vector comprises other elements in addition to the cell-specific nuclear targeting molecule and the nucleic acid sequence of interest. In some embodiments, a bacterial origin of replication (such as ori C for replication in *Escherichia coli*, or the origin of replication of *Bacillus subtilis* for replication therein, or the origin of replication of *Pseudomonas aeruginosa* for replication therein, etc.) is included to maintain the vector in a bacterial host. In some embodiments, such an embodiment of the vector of the subject invention includes a selection marker for selecting bacterial colonies that contain the subject vector. Such selectable or biological markers are well known in the art. In bacteria, these are commonly drug-resistance genes. Drug or antibiotic resistance is used to select bacteria that have taken up cloned DNA from the much larger population of bacteria that have not.

A selection marker can also be included in the vector to identify mammalian cells that have taken up the vector DNA. In some embodiments, the herpes simplex virus thymidine kinase (HSV tk) gene is used as a selectable genetic marker in mammalian cells in much the same way that drug-resistance genes work in bacteria, to allow rare transfected cells to grow up out of a much larger population that did not take up any DNA. The cells are transferred to selective growth medium, which permits growth only of cells that took up a functional tk gene (and the transferred DNA of interest). Various dominant selectable markers are now known in the art, including, but not limited to, aminoglycoside phosphotransferase (APH), using the drug G418 for selection which inhibits protein synthesis; the APH inactivates G418; dihydrofolate reductase (DHFR):Mtx-resistant variant, using the drug methotrexate (Mtx) for selection which inhibits DHFR; the variant DHFR is resistant to Mtx; hygromycin-B-phosphotransferase (HPH), using the drug hygromycin-B which inhibits protein synthesis; the HPH inactivates hygromycin B; thymidine kinase (TK), using the drug aminopterin which inhibits de novo purine and thymidylate synthesis; the TK synthesizes thymidylate; xanthine-guanine phosphoribosyltransferase (XGPRT), using the drug mycophenolic acid which inhibits de novo GMP synthesis; XGPRT synthesizes GMP from xanthine; adenosine deaminase (ADA), using the drug 9-.beta.-D-xylofuranosyl adenine (Xyl-A) which damages DNA; the ADA inactivates Xyl-A; and multidrug resistance (MDR), which is also known as the P-glycoprotein (Licht et al. 1995).

In other embodiments, gene amplification is used to obtain very high levels of expression of transfected genes. When cell cultures are treated with Mtx, an inhibitor of a critical metabolic enzyme, DHFR, most cells die, but eventually some Mtx-resistant cells grow up. A gene to be expressed in cells is cotransfected with a cloned dhfr gene, and the transfected cells are subjected to selection with a low concentration of Mtx. Resistant cells that have taken up the dhfr gene (and, in most cases, the cotransfected gene) multiply. Increasing the concentration of Mtx in the growth medium in small steps generates populations of cells that have progressively amplified the dhfr gene, together with linked DNA. The resulting cell cultures capable of growing in the highest Mtx concentrations will have stably amplified the DNA encompassing the dhfr gene a hundredfold or more, leading to significant elevation of the expression of the cotransfected gene.

In yet other embodiments, the vectors of the present invention include a promoter or enhancer sequence to control expression of the DNA molecule to be targeted. In some embodiments, such a promoter sequence is positioned upstream from the DNA molecule in order to effectively control expression of the DNA molecule. RNA polymerase normally binds to the promoter and initiates transcription of a gene (the DNA molecule) or a group of linked genes and regulatory elements (operon). Promoters vary in their strength, i.e., ability to promote transcription. For the purpose of expressing a nucleic acid sequence of interest, it is preferred to use strong promoters in order to obtain a high level of transcription and, hence, expression of the gene or RNA encoded by the nucleic acid sequence of interest. In other embodiments, the promoter is a tissue-specific promoter that only turns on in the correct tissue, or a developmentally regulated promoter that only turns on at a certain time in the development of a cell or tissue. Examples include the alpha-actin promoter, which is expressed in muscle cells (Shimizu et al., J. Biol. Chem. 270:7631 (1995)), the beta globin promoter, which is expressed in adult erythrocyte progenitor cells, or the gamma globin promoter, which is expressed in fetal erythrocyte progenitor cells. Depending upon the host cell system utilized, any one of a number of suitable promoters can be used. In bacterial host cells, suitable promoters include, for example, the lac promoter, trp promoter, recA promoter, ribosomal RNA promoter, the $P_R$ and $P_L$ promoters of coliphage lambda, and others, including but not limited to, lacUV5, ompF, bla, lpp and the like, and the nos promoter. Additionally, a hybrid trp-lacUV5 (tac) promoter or other *E. coli* promoters produced by recombinant DNA or other synthetic DNA techniques can be used to provide for transcription of the DNA molecule of the invention. Other promoters for use in plant cells include, for example, the small subunit chlorophyll A/B binding polypeptide, the 35S promoter of cauliflower mosaic virus, and promoters isolated from plant genes, including the Pto promoter itself (Vallejos et al. 1986) to direct high levels of transcription of adjacent DNA segments. Suitable promoters for expression of genes in animal cells include, for example, the beta-actin promoter, cytomegalovirus (CMV) promoter, Adenovirus major late promoter, Thymidylate kinase (TK) promoter, and the Rous Sarcoma Virus (RSV) LTR-promoter. An example of a suitable promoter for use in insect cells is the AcMNPV polyhedrin promoter.

In some embodiments, bacterial host cell strains and expression vectors are chosen that inhibit the action of the promoter unless specifically induced. In certain operons the addition of specific inducers is necessary for efficient transcription of the inserted DNA; for example, the lac operon is induced by the addition of lactose or IPTG (isopropylthio-beta-D-galactoside). A variety of other operons, such as trp, pro, etc., are under different controls. The trp operon is induced when tryptophan is absent in the growth media; and the $P_L$ promoter of lambda can be induced by an increase in temperature in host cells containing a temperature sensitive lambda repressor, e.g., c1857. In this way, greater than 95% of the promoter-directed transcription is inhibited in uninduced cells. Thus, expression of the DNA molecule of the invention can be controlled.

When cloning in a eukaryotic host cell, enhancer sequences (e.g., the enhancer from the CMV immediate early promoter or the retroviral long terminal repeats (LTRs), etc.) may be inserted to increase transcriptional efficiency. Enhancer sequences are a set of eukaryotic DNA elements that to increase transcriptional efficiency in a manner relatively independent of their position and orientation with respect to a nearby gene.

Specific initiation signals are also required for efficient gene transcription and translation in prokaryotic cells. These transcription and translation initiation signals vary in "strength" as measured by the quantity of gene specific messenger RNA and protein synthesized, respectively. The DNA expression vector, which contains a promoter, may also contain any combination of various "strong" transcription and/or translation initiation signals. For instance, efficient translation in *E. coli* requires a Shine-Dalgarno (SD) sequence about 7-9 bases 5' to the initiation codon (ATG) to provide a ribosomal binding site. Thus, any SD-ATG combination that can be utilized by host cell ribosomes can be employed. Such combinations include but are not limited to the SD-ATG combination from the CRO gene or the N gene of coliphage lambda, or from the *E. coli* tryptophan E, D, C, B or A genes. Additionally, any SD-ATG combination produced by recombinant DNA or other techniques involving incorporation of synthetic nucleotides can be used.

In accordance with the subject invention, the nucleic acid sequence of interest is targeted into the nuclei of the specific cell type (e.g., pulmonary cells), where the nucleic acid sequence of interest is expressed. In some embodiments, since the nuclear-localized plasmid DNA will eventually be degraded, it is preferred for long term expression of the DNA molecule in the nuclei of the specific cell type to integrate the nucleic acid sequence of interest into the genome of the specific cell type. In such an embodiment, the vector further includes a molecule to direct integration of the nucleic acid sequence of interest into the genome of the specific cell type. Such integration sequences are known in the art, and include, for example, the inverted terminal repeats of adeno-associated virus (ITRs), retroviral long terminal repeats (LTRs), cre/lox and phiC31 integrase sites, and other viral sequences shown to cause incorporation or integration of the viral genome into the specific cell type genome.

Various additional elements can be included in the vector of the subject invention depending upon the desired goal. For ease in constructing various embodiments of the vector, the vector can also contain a number of unique restriction enzyme sites for insertion of the additional molecules or elements. As used herein, a "unique" restriction enzyme site refers to the presence of only one cleavage site for a particular restriction endonuclease within the plasmid DNA. That particular restriction endonuclease (or restriction enzyme) will, therefore, only cleave the DNA of the plasmid at that one location or "unique" site. These unique restriction sites can be provided in the plasmid of the subject invention by including a polylinker as an element of the vector. The vector of the subject invention may also contain restriction sites that occur twice in close proximity (i.e., the flanking sites of the polylinker) and these could also be used to clone in sequence between the sites.

The present invention further provides a host cell comprising the vector of the present invention. As indicated above, for maintenance and propagation of the plasmid, a bacterial host cell (such as *Escherichia coli*) is preferred. Bacterial host cells for maintenance and propagation offer the advantages of being easy to work with and capable of rapid reproduction and therefore propagation of the vector.

In some embodiments, the nucleic acid sequence of interest is targeted to the nucleus of a specific cell type in an animal (including, for example, mammals, birds, amphibians, reptiles and fish). Suitable host cells are any cells into which a nucleic acid sequence of interest is desired to be introduced. For example, and referring to the many possible uses of the subject invention discussed below and above, the host cell may be a pulmonary epithelial cell where gene therapy of cystic fibrosis lung disease is being treated and/or prevented. Many other suitable host cells should be readily apparent, as the invention has broad applicability to various host cells and various DNA molecules to be imported into the nucleus thereof. In other embodiments, the host cell is in vitro (e.g., including, but not limited to, the mammalian cells identified as NIH3T3 cells, Hela cells, COS cells, and CHO cells, and the insect cell lines identified as Drosophila Schneider, Drosophila $K_C$, and Sf9).

In other embodiments, a viral vector is used to introducing the vector into the host cell. For example, in some embodiments, the viral vector is an adenovirus, retrovirus, adeno-associated virus, vaccinia virus, papovavirus, or herpes simplex virus vector. In other embodiments, an insect virus, such as baculovirus, is used for introduction into an insect cell, or a plant virus for introduction into a plant cell.

The nuclear targeting molecule of the subject invention also offers the advantage of being able to target a DNA molecule to the nucleus of a non-dividing host cell. Non-dividing cells include two classes of cells: those that are not dividing (quiescent) and those that cannot divide (i.e., many terminally differentiated cell types). When cells leave mitosis and are finished dividing, they enter the G1 phase of the cell cycle and then come to a halt at G0 (G zero). At this point they are "growth-arrested"; protein synthesis is decreased as is transcription. Upon stimulation, most cells will exit G0 and continue on with the cell cycle, leading to division. However, many cells will remain in this G0 state for a long time. Human liver cells, in the absence of liver damage, will divide only once or twice a year while gut epithelia will divide twice a day. The period of quiescence for each type of cell is different, but if it is greater than 48 hours, the method of the subject invention is especially applicable.

As examples of quiescent cells are hematopoeitic stem cells (CD34+ cells). These cells have the potential to divide and self-renew, but they are normally quiescent until stimulated to divide. These cells are desired targets for gene therapy (sickle cell disease, thalassemia, SCID), and the subject method provides a method to get DNA into the cells even though they normally do not divide. Other quiescent cells include fibroblasts in the absence of tissue damage, liver cells in the absence of liver damage, and skeletal muscle cells (these are classic "post-mitotic cells"). Non-dividing, terminally-differentiated cells are sometimes called "Permanent cells". Many cells are produced during embryogenesis in numbers that will suffice for the lifetime of the organism. Thus, once they divide and differentiate, they will never divide again. These terminally-differentiated or permanent cells include most neurons and nerve cells; non-dividing differentiated epithelial cells (i.e., top layers of skin that are still living or villus cells of the gut lumen); muscle cells of the heart; auditory hair cells of the ear; and lens cells of the eye.

Various methods are known in the art for introducing nucleic acid molecules into host cells (including the specific cell type). In some embodiments, microinjection, in which DNA is injected directly into the cytoplasm of cells through fine glass needles is used. In other embodiments, DNA is incubated with an inert carbohydrate polymer (dextran) to which a positively charged chemical group (DEAE, for diethylaminoethyl) has been coupled. The DNA sticks to the DEAE-dextran via its negatively charged phosphate groups. These large DNA-containing particles stick in turn to the surfaces of cells, which are thought to take them in by a process known as endocytosis. In another method, cells efficiently take in DNA in the form of a precipitate with calcium phosphate. In electroporation, cells are placed in a solution containing DNA and subjected to a brief electrical pulse that causes holes to open transiently in their membranes. DNA enters through the holes directly into the cytoplasm, bypassing the endocytotic vesicles through which they pass in the DEAE-dextran and calcium phosphate procedures (passage through these vesicles may sometimes destroy or damage DNA). In other embodiments, vector DNA is incorporated into artificial lipid vesicles, liposomes, which fuse with the cell membrane, delivering their contents directly into the cytoplasm. In still further embodiments, DNA is absorbed to the surface of tungsten microprojectiles and fired into cells with a device resembling a shotgun.

Electroporation is a transformation method in which, generally, a high concentration of vector DNA is added to a suspension of host cell protoplasts, yeast, animal cells, bacterial cells, or animals, and the mixture shocked with an electrical field of 200 to 600 V/cm. Following electroporation, transformed cells are identified by growth on appropriate medium containing a selective agent.

Particle bombardment (also know as biolistic transformation) of the host cell can be accomplished in one of several ways. The first involves propelling inert or biologically active particles at cells. This technique is disclosed in U.S. Pat. Nos. 4,945,050, 5,036,006, and 5,100,792, all to Sanford et al., which are hereby incorporated by reference. Generally, this procedure involves propelling inert or biologically active particles at the cells under conditions effective to penetrate the outer surface of the cell and to be incorporated within the interior thereof. When inert particles are utilized, the vector can be introduced into the cell by coating the particles with the vector. Alternatively, the target cell can be surrounded by the vector so that the vector is carried into the cell by the wake of the particle. In further embodiments, a cell or tissue is transfected ex vivo and subsequently transplanted into a host organism.

The present invention is not limited to the vectors described herein. Specific vectors suitable for use in a variety of applications are described in more detail below. One skilled in the relevant art recognizes that modifications and additions to the vectors described herein may be included for certain applications.

II. Gene Therapy Applications

In some embodiments, the present invention also provides methods and compositions utilizing the nuclear targeting signals of the present invention that are suitable for gene therapy to alter expression of a gene of interest for research, drug screening, therapeutic applications, etc. In some embodiments, the gene therapy applications are used to replace a gene whose expression is down-regulated in a cell of interest (e.g., a lung cell). In other embodiments, gene therapy is used to replace a defective copy of a gene of interest. In still further embodiments, gene therapy is used to down-regulate the expression of a gene that is overexpressed (e.g., through the use of antisense or siRNA technologies). Such applications find use in the treatment of disease (e.g., lung disease) characterized by the aberrant expression of a gene or the presence of a defective copy of a gene.

Viral vectors commonly used for in vivo or ex vivo targeting and therapy procedures are, for example, DNA-based vectors and retroviral vectors. Methods for constructing and using viral vectors are known in the art (See e.g., Miller and Rosman, BioTech., 7:980-990 [1992]). Preferably, the viral vectors are replication defective, that is, they are unable to replicate autonomously in the target cell. In general, the genome of the replication defective viral vectors that are used within the scope of the present invention lack at least one region that is necessary for the replication of the virus in the infected cell. These regions can either be eliminated (in whole or in part), or be rendered non-functional by any technique known to a person skilled in the art. These techniques include the total removal, substitution (by other sequences, in particular by the inserted nucleic acid), partial deletion or addition of one or more bases to an essential (for replication) region. Such techniques may be performed in vitro (i.e., on the isolated DNA) or in situ, using the techniques of genetic manipulation or by treatment with mutagenic agents.

Preferably, the replication defective virus retains the sequences of its genome that are necessary for encapsidating the viral particles. DNA viral vectors include an attenuated or defective DNA viruses, including, but not limited to, herpes simplex virus (HSV), papillomavirus, Epstein Barr virus (EBV), adenovirus, adeno-associated virus (AAV), and the like. Defective viruses, that entirely or almost entirely lack viral genes, are preferred, as defective virus is not infective after introduction into a cell. Use of defective viral vectors allows for administration to cells in a specific, localized area, without concern that the vector can infect other cells. Thus, a specific tissue can be specifically targeted. Examples of particular vectors include, but are not limited to, a defective herpes virus 1 (HSV1) vector (Kaplitt et al., Mol. Cell. Neurosci., 2:320-330 [1991]), defective herpes virus vector lacking a glycoprotein L gene (See e.g., Patent Publication RD 371005 A), or other defective herpes virus vectors (See e.g., WO 94/21807; and WO 92/05263); an attenuated adenovirus vector, such as the vector described by Stratford-Perricaudet et al. (J. Clin. Invest., 90:626-630 [1992]; See also, La Salle et al., Science 259:988-990 [1993]); and a defective adeno-associated virus vector (Samulski et al., J. Virol., 61:3096-3101 [1987]; Samulski et al., J. Virol., 63:3822-3828 [1989]; and Lebkowski et al., Mol. Cell. Biol., 8:3988-3996 [1988]).

Preferably, for in vivo administration, an appropriate immunosuppressive treatment is employed in conjunction with the viral vector (e.g., adenovirus vector), to avoid immuno-deactivation of the viral vector and transfected cells. For example, immunosuppressive cytokines, such as interleukin-12 (IL-12), interferon-gamma (IFN-γ), or anti-CD4 antibody, can be administered to block humoral or cellular immune responses to the viral vectors. In addition, it is advantageous to employ a viral vector that is engineered to express a minimal number of antigens.

In a preferred embodiment, the vector is an adenovirus vector. Adenoviruses are eukaryotic DNA viruses that can be modified to efficiently deliver a nucleic acid of the invention to a variety of cell types. Various serotypes of adenovirus exist. Of these serotypes, preference is given, within the scope of the present invention, to type 2 or type 5 human adenoviruses (Ad 2 or Ad 5), or adenoviruses of animal origin (See e.g., WO94/26914). Those adenoviruses of animal origin that can be used within the scope of the present invention include adenoviruses of canine, bovine, murine (e.g., Mav1, Beard et al., Virol., 75-81 [1990]), ovine, porcine, avian, and simian (e.g., SAV) origin. Preferably, the adenovirus of animal origin is a canine adenovirus, more preferably a CAV2 adenovirus (e.g. Manhattan or A26/61 strain (ATCC VR-800)).

Preferably, the replication defective adenoviral vectors of the invention comprise the ITRs, an encapsidation sequence and the nucleic acid of interest. Still more preferably, at least the E1 region of the adenoviral vector is non-functional. The deletion in the E1 region preferably extends from nucleotides 455 to 3329 in the sequence of the Ad5 adenovirus (PvuII-BglII fragment) or 382 to 3446 (HinfII-Sau3A fragment). Other regions may also be modified, in particular the E3 region (e.g., WO95/02697), the E2 region (e.g., WO94/28938), the E4 region (e.g., WO94/28152, WO94/12649 and WO95/02697), or in any of the late genes L1-L5.

In a preferred embodiment, the adenoviral vector has a deletion in the E1 region (Ad 1.0). Examples of E1-deleted adenoviruses are disclosed in EP 185,573, the contents of which are incorporated herein by reference. In another preferred embodiment, the adenoviral vector has a deletion in the E1 and E4 regions (Ad 3.0). Examples of E1/E4-deleted adenoviruses are disclosed in WO95/02697 and WO96/22378. In still another preferred embodiment, the adenoviral vector has a deletion in the E1 region into which the E4 region and the nucleic acid sequence are inserted.

The replication defective recombinant adenoviruses according to the invention can be prepared by any technique known to the person skilled in the art (See e.g., Levrero et al., Gene 101:195 [1991]; EP 185 573; and Graham, EMBO J., 3:2917 [1984]). In particular, they can be prepared by homologous recombination between an adenovirus and a plasmid, which carries, inter alia, the DNA sequence of interest. The homologous recombination is accomplished following co-transfection of the adenovirus and plasmid into an appropriate cell line. The cell line that is employed should preferably (i) be transformable by the elements to be used, and (ii) contain the sequences that are able to complement the part of the genome of the replication defective adenovirus, preferably in integrated form in order to avoid the risks of recombination. Examples of cell lines that may be used are the human embryonic kidney cell line 293 (Graham et al., J. Gen. Virol., 36:59 [1977]), which contains the left-hand portion of the genome of an Ad5 adenovirus (12%) integrated into its genome, and cell lines that are able to complement the E1 and E4 functions, as described in applications WO94/26914 and WO95/02697. Recombinant adenoviruses are recovered and purified using standard molecular biological techniques that are well known to one of ordinary skill in the art.

The adeno-associated viruses (AAV) are DNA viruses of relatively small size that can integrate, in a stable and site-specific manner, into the genome of the cells that they infect. They are able to infect a wide spectrum of cells without inducing any effects on cellular growth, morphology or differentiation, and they do not appear to be involved in human pathologies. The AAV genome has been cloned, sequenced and characterized. It encompasses approximately 4700 bases and contains an inverted terminal repeat (ITR) region of approximately 145 bases at each end, which serves as an origin of replication for the virus. The remainder of the genome is divided into two essential regions that carry the encapsidation functions: the left-hand part of the genome, that contains the rep gene involved in viral replication and expression of the viral genes; and the right-hand part of the genome, that contains the cap gene encoding the capsid proteins of the virus.

The use of vectors derived from the AAVs for transferring genes in vitro and in vivo has been described (See e.g., WO 91/18088; WO 93/09239; U.S. Pat. No. 4,797,368; U.S. Pat. No. 5,139,941; and EP 488 528, all of which are herein incorporated by reference). These publications describe various AAV-derived constructs in which the rep and/or cap genes are deleted and replaced by a gene of interest, and the use of these constructs for transferring the gene of interest in vitro (into cultured cells) or in vivo (directly into an organism). The replication defective recombinant AAVs according to the invention can be prepared by co-transfecting a plasmid containing the nucleic acid sequence of interest flanked by two AAV inverted terminal repeat (ITR) regions, and a plasmid carrying the AAV encapsidation genes (rep and cap genes), into a cell line that is infected with a human helper virus (for example an adenovirus). The AAV recombinants that are produced are then purified by standard techniques.

In another embodiment, the gene can be introduced in a retroviral vector (e.g., as described in U.S. Pat. Nos. 5,399, 346, 4,650,764, 4,980,289 and 5,124,263; all of which are herein incorporated by reference; Mann et al., Cell 33:153 [1983]; Markowitz et al., J. Virol., 62:1120 [1988]; PCT/US95/14575; EP 453242; EP178220; Bernstein et al. Genet. Eng., 7:235 [1985]; McCormick, BioTechnol., 3:689 [1985]; WO 95/07358; and Kuo et al., Blood 82:845 [1993]). The retroviruses are integrating viruses that infect dividing cells. The retrovirus genome includes two LTRs, an encapsidation sequence and three coding regions (gag, pol and env). In recombinant retroviral vectors, the gag, pol and env genes are generally deleted, in whole or in part, and replaced with a heterologous nucleic acid sequence of interest. These vectors can be constructed from different types of retrovirus, such as, HIV, MoMuLV ("murine Moloney leukemia virus" MSV ("murine Moloney sarcoma virus"), HaSV ("Harvey sarcoma virus"); SNV ("spleen necrosis virus"); RSV ("Rous sarcoma virus") and Friend virus. Defective retroviral vectors are also disclosed in WO95/02697.

In general, in order to construct recombinant retroviruses containing a nucleic acid sequence, a plasmid is constructed that contains the LTRs, the encapsidation sequence and the construct of the present invention comprising a nuclear targeting signal and a coding sequence. This construct is used to transfect a packaging cell line, which cell line is able to supply in trans the retroviral functions that are deficient in the plasmid. In general, the packaging cell lines are thus able to express the gag, pol and env genes. Such packaging cell lines have been described in the prior art, in particular the cell line PA317 (U.S. Pat. No. 4,861,719, herein incorporated by reference), the PsiCRIP cell line (See, WO90/02806), and the GP+envAm-12 cell line (See, WO89/07150). In addition, the recombinant retroviral vectors can contain modifications within the LTRs for suppressing transcriptional activity as well as extensive encapsidation sequences that may include a part of the gag gene (Bender et al., J. Virol., 61:1639 [1987]). Recombinant retroviral vectors are purified by standard techniques known to those having ordinary skill in the art.

Alternatively, the vector can be introduced in vivo by lipofection. For the past decade, there has been increasing use of liposomes for encapsulation and transfection of nucleic acids in vitro. Synthetic cationic lipids designed to limit the difficulties and dangers encountered with liposome mediated transfection can be used to prepare liposomes for in vivo transfection of a gene encoding a marker (Felgner et. al., Proc. Natl. Acad. Sci. USA 84:7413-7417 [1987]; See also, Mackey, et al., Proc. Natl. Acad. Sci. USA 85:8027-8031 [1988]; Ulmer et al., Science 259:1745-1748 [1993]). The use of cationic lipids may promote encapsulation of negatively charged nucleic acids, and also promote fusion with negatively charged cell membranes (Felgner and Ringold, Science 337:387-388 [1989]). Particularly useful lipid compounds and compositions for transfer of nucleic acids are described in WO95/18863 and WO96/17823, and in U.S. Pat. No. 5,459, 127, herein incorporated by reference.

Other molecules are also useful for facilitating transfection of a nucleic acid in vivo, such as a cationic oligopeptide (e.g., WO95/21931), peptides derived from DNA binding proteins (e.g., WO96/25508), or a cationic polymer (e.g., WO95/21931).

It is also possible to introduce the vector in vivo as a naked DNA plasmid. Methods for formulating and administering naked DNA to mammalian muscle tissue are disclosed in U.S. Pat. Nos. 5,580,859 and 5,589,466, both of which are herein incorporated by reference.

DNA vectors for gene therapy can be introduced into the desired host cells by methods known in the art, including but not limited to transfection, electroporation, microinjection, transduction, cell fusion, DEAE dextran, calcium phosphate precipitation, use of a gene gun, or use of a DNA vector transporter (See e.g., Wu et al., J. Biol. Chem., 267:963-967 [1992]; Wu and Wu, J. Biol. Chem., 263:14621-14624 [1988]; and Williams et al., Proc. Natl. Acad. Sci. USA 88:2726-2730 [1991]). Receptor-mediated DNA delivery approaches can also be used (Curiel et al., Hum. Gene Ther., 3:147-154 [1992]; and Wu and Wu, J. Biol. Chem., 262:4429-4432 [1987]).

III. Drug Screening Applications

In other embodiments, the constructs of the present invention find use in drug screening. For example, in some embodiments, the methods of the present invention are used to generate cells (e.g., lung cells) that express or repress expression of a gene of interest. In some embodiments, the cell is in a non-human animal (e.g., non-human mammal). In other embodiments, the cell is in culture. In preferred embodiments, the expression of the nucleic acid encoded by the construct of the present invention generates a cell or animal that mimics a disease state. Test compounds are then administered to the cell or animal and the effect of the test compounds on the disease state is monitored.

The test compounds of the present invention can be obtained using any of the numerous approaches in combinatorial library methods known in the art, including biological libraries; peptoid libraries (libraries of molecules having the functionalities of peptides, but with a novel, non-peptide backbone, which are resistant to enzymatic degradation but which nevertheless remain bioactive; see, e.g., Zuckermann et al., J. Med. Chem. 37: 2678-85 [1994]); spatially addressable parallel solid phase or solution phase libraries; synthetic library methods requiring deconvolution; the 'one-bead one-compound' library method; and synthetic library methods using affinity chromatography selection. The biological library and peptoid library approaches are preferred for use with peptide libraries, while the other four approaches are applicable to peptide, non-peptide oligomer or small molecule libraries of compounds (Lam (1997) Anticancer Drug Des. 12:145).

Examples of methods for the synthesis of molecular libraries can be found in the art, for example in: DeWitt et al., Proc. Natl. Acad. Sci. U.S.A. 90:6909 [1993]; Erb et al., Proc. Nad. Acad. Sci. USA 91:11422 [1994]; Zuckermann et al., J. Med. Chem. 37:2678 [1994]; Cho et al., Science 261:1303 [1993]; Carrell et al., Angew. Chem. Int. Ed. Engl. 33.2059 [1994]; Carell et al., Angew. Chem. Int. Ed. Engl. 33:2061 [1994]; and Gallop et al., J. Med. Chem. 37:1233 [1994].

Libraries of compounds may be presented in solution (e.g., Houghten, Biotechniques 13:412-421 [1992]), or on beads (Lam, Nature 354:82-84 [1991]), chips (Fodor, Nature 364: 555-556 [1993]), bacteria or spores (U.S. Pat. No. 5,223,409; herein incorporated by reference), plasmids (Cull et al., Proc. Nad. Acad. Sci. USA 89:18651869 [1992]) or on phage (Scott and Smith, Science 249:386-390 [1990]; Devlin Science 249: 404-406 [1990]; Cwirla et al., Proc. Natl. Acad. Sci. 87:6378-6382 [1990]; Felici, J. Mol. Biol. 222:301 [1991]).

IV. Additional Research Applications

The present invention is not limited to the drug screening and gene therapy applications described above. As described above, the constructs of the present invention can be used to generate cells or animals that mimic a disease state. The methods of the present invention can be used in research application to further elucidate disease or metabolic pathways (e.g., through altering expression of a gene of interest and monitoring the resulting phenotype). In some embodiments, disease states are mimicked by reducing expression of a gene of interest (e.g., through antisense or siRNA applications).

EXPERIMENTAL

The following examples are provided in order to demonstrate and further illustrate certain preferred embodiments and aspects of the present invention and are not to be construed as limiting the scope thereof.

EXAMPLE 1

The human SP-C promoter (−318 to +46) mediates plasmid nuclear import in alveolvar epithelial cells Experiments conducted during the course of development of the present invention utilized the promoters of several human genes in order to identify signal sequences for specifically targeting lung epithelial cells. These promoters were selected based on their transcription specificity within the targeted lung cell type. The surfactant protein (SP-A, SP-B, SP-C, SP-D) promoters were selected for analysis, as well as the promoter elements of keratins 8 and 18. (Table 1.)

TABLE 1

| Alveolar Epithelial Genes Tested | | |
|---|---|---|
| Gene | Promoter Fragment | Reference |
| SP-A1 | −1000 to +38 | Kouretas et al, 1993 |
| SP-A2 | −1174 to +1 | N/A |
| SP-B | −730 to +39 | Bohinski et al, 1993 |
| SP-C | −318 to +18 | Glasser et al, 2000 |
| SP-D | −1675 to +864 | Rust et al, 1996 |
| K-8 | −1762 to +18 | N/A |
| K-18 | −2580 to +750 | Chow et al, 1997 |

These promoter sequences were amplified by PCR using primers designed based on the Genbank sequences of the various promoters and cloned into a pTA-TOPO vector (Invitrogen Co., Carlsbad, Calif.), using standard techniques. To assay for nuclear import, the promoter-containing plasmids were cytoplasmically injected into A549 (human lung adenocarcinoma) cells along with rhodamine-labeled bovine serum albumin (Rh-BSA). The cells were fixed 8 hours post-injection, and the localization of the plasmid DNA visualized using in situ hybridization. Rh-BSA is only able to access the nucleus if accidentally injected into the nucleus, or if the cells had undergone division. Hence, cells with nuclear Rh-BSA were not scored. Plasmids containing the SP-A, SP-B, SP-D, keratin-8 and keratin-18 promoters remained in the cytoplasm of injected cells, indicating that they cannot enter the nucleus of non-dividing cells. By contrast, plasmids containing the 365 bp human SP-C promoter (−318 to +47; SEQ ID:1) localized to the nuclei of non-dividing cells by 8 hours following cytoplasmic microinjection. Between 500 and 1000 cells were microinjected and analyzed for each plasmid. Representative cells are shown. (FIG. 2.) These results demonstrate that the SP-C promoter has DNA nuclear targeting activity.

EXAMPLE 2

The human SP-C promoter (−318 to +46) does not mediate plasmid nuclear import in other cell types.

Figure 3:
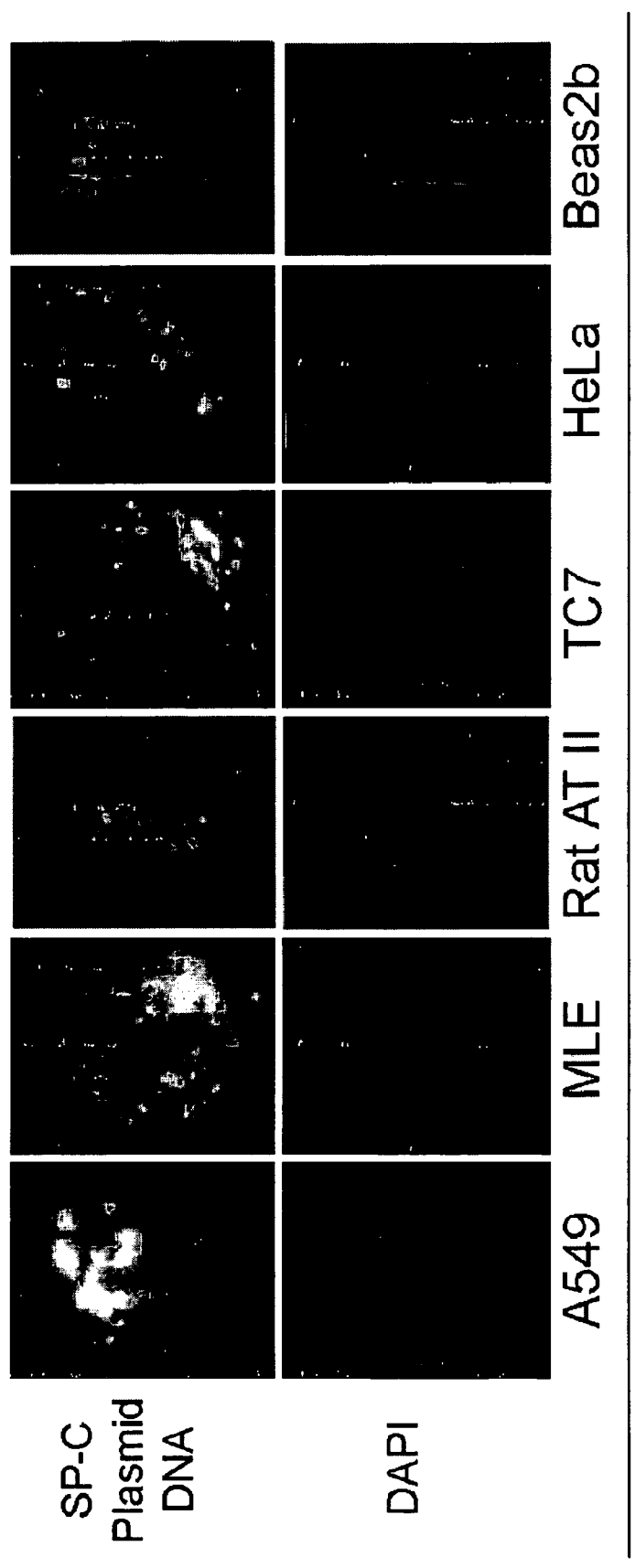
FIG. 3 depicts cells from distinct epithelial lines that have been cytoplasmically injected with plasmids containing the 336 bp SP-C promoter, showing sequence- and cell-specific nuclear import of SP-C plasmid DNA.

In order to determine whether the nuclear import activity of the human SP-C promoter (−318 to +46) is specific to pulmonary epithelial cells, identical experiments were conducted in other epithelial cell lines from different tissues. The nuclear targeting of the pCRII-TOPO plasmid (Invitrogen Co., Carlsbad, Calif.) containing the SP-C promoter was assayed using the microinjection strategy described above in non-AEC lines. Upon injection of the SP-C containing GFP plasmid into HeLa cells (human epithelial cells from a cervical carcinoma), TC7 cells (African Green Monkey Kidney epithelial cell), ATII cells (primary rat alveolar epithelial type 2 cells), MLE cells (murine lung epithelial type II-derived cells), and Beas-2B (bovine airway epithelial cells), no increased numbers of GFP-expressing cells were observed versus empty vector controls. (FIG. 3.) In all cases, the numbers of GFP-expressing cells were less than that seen when the SP-C construct was injected into A549 or MLE cells. Thus, the SP-C promoter confers cell-type specific nuclear import into pulmonary alveolar epithelial cells, but not in other cell types investigated.

EXAMPLE 3

Figure 4:
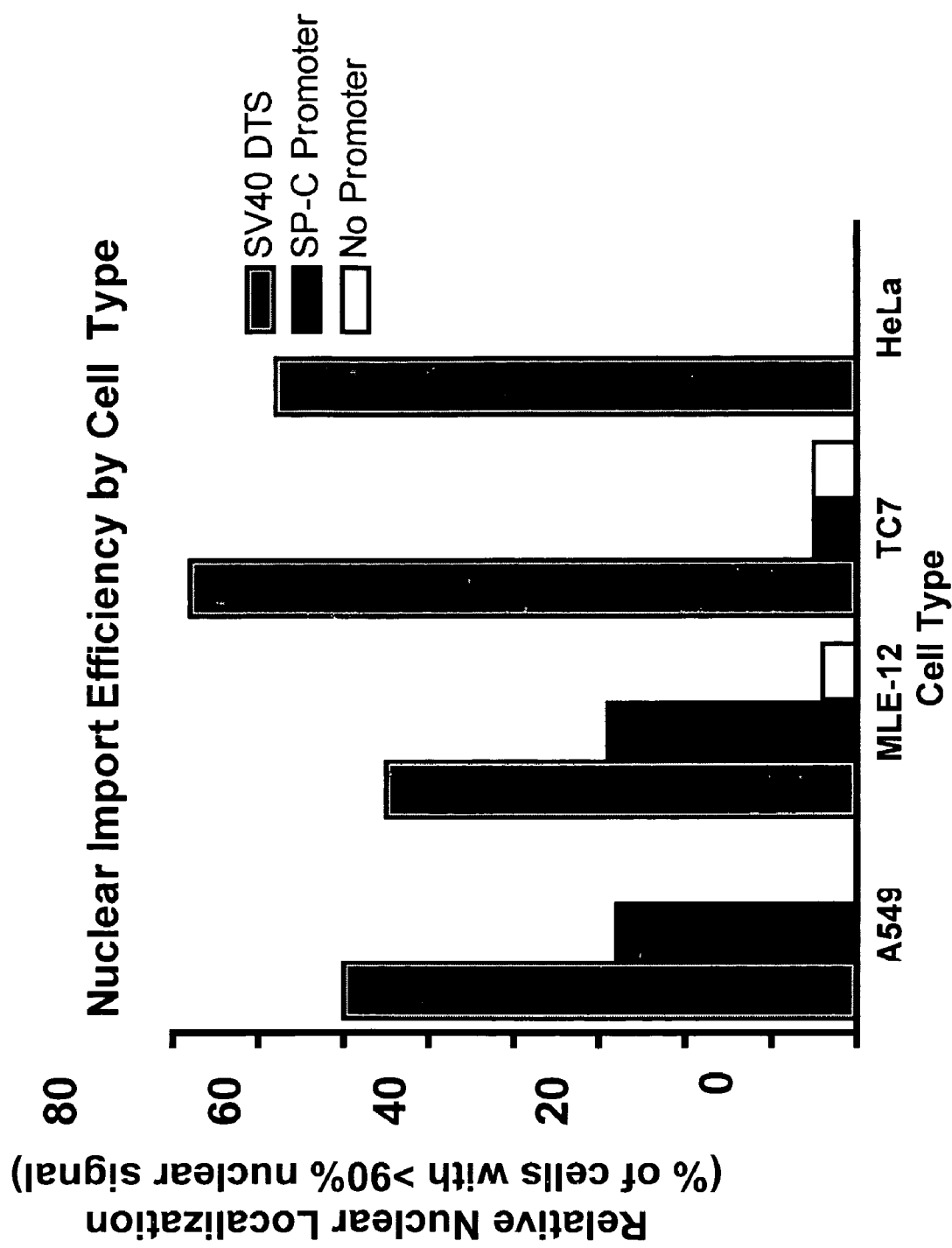
FIG. 4 is a bar graph showing the relative efficiency of nuclear import of plasmids containing the SP-C promoter by cell type.

The human SP-C promoter (−318 to +46)-mediated plasmid nuclear import is efficient and quantitative To establish the efficiency of transgene nuclear import and to quantify the results, the SP-C promoter was cloned into a GFP expression plasmid downstream of the CMV promoter-driven GFP reporter gene so as to not affect transcriptional activity. For GFP to be expressed, the plasmid must first enter the nucleus and then be transcribed. Without an appropriate DNA targeting sequence the plasmid cannot enter the nucleus prior to cell division. Thus, only cells with the DNA targeting sequence express GFP at 8 hours. Five hundred to 1000 cells in 5 separate experiments were cytoplasmically microinjected with plasmids containing the SP-C promoter and GFP was assayed 8 hours later. GFP expression was detected in 29.6%±9.8% of viable A549 cells, much higher than control plasmid lacking DNA targeting sequence (1.0%±2.9%). (FIG. 4.) Similar results were seen in murine lung epithelial type II-derived (MLE) cells, thereby confirming that nuclear import is mediated by the SP-C promoter.

EXAMPLE 4

Figure 5:
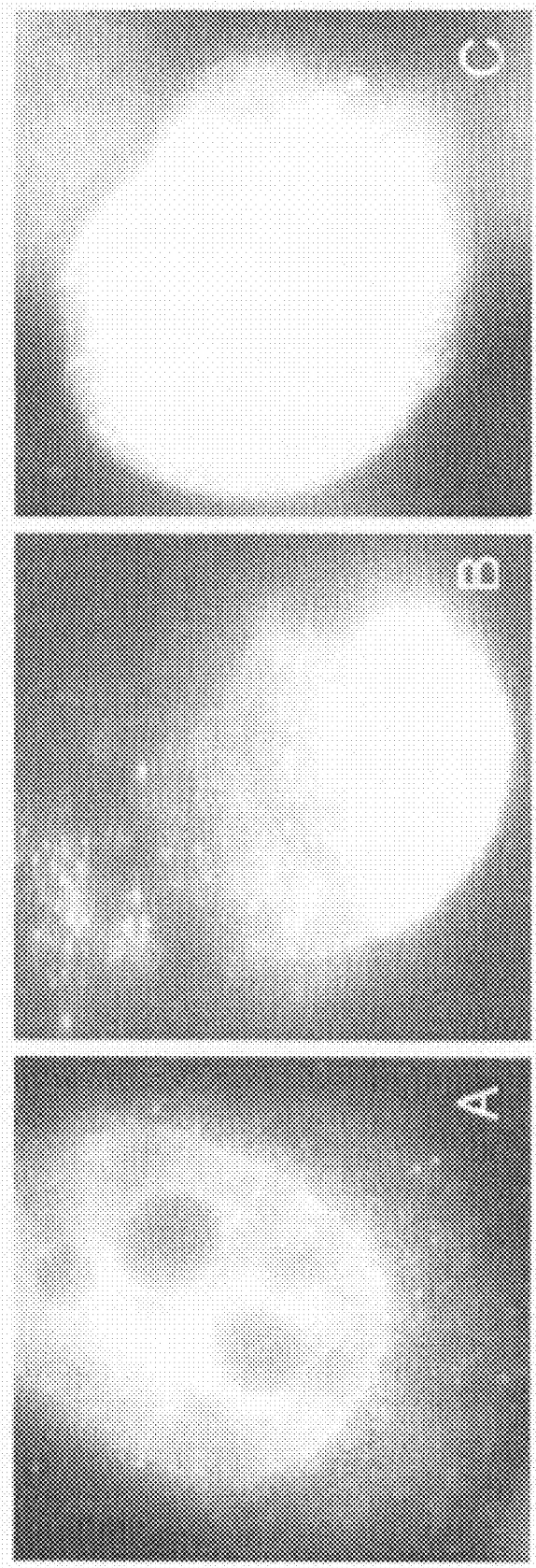
FIG. 5 shows the intracellular fate of plasmids containing the SP-C promoter DNA nuclear targeting sequence (DTS) that have been labeled with 3-10 PNAs per plasmid, and microinjected into the cytoplasm of A549 cells.

PNA-labeled plasmid DNA coupled to the human SP-C promoter (−318 to +46) enters the nucleus To observe the fate of extrinsic plasmid DNA in living cells, plasmids labeled with peptide nucleic acids (PNAs) clamps were used. PNAs form a stable triplex structure with plasmid DNA, and when labeled with fluorescent molecules are able to track plasmid DNA transport in real-time through, for example, nuclear import and transcription. To verify that PNA-labeled plasmid DNA enters the nucleus, and to serve as a high-resolution assay for SP-C plasmid localization, plasmids containing the SP-C promoter DNA nuclear targeting sequence (DTS) were labeled with 3-10 PNAs per plasmid, and microinjected into the cytoplasm of A549 cells. The DNA was observed using fluorescence microscopy over an 8 hour period, and the amount of DNA located in the nuclear and in the cytoplasmic compartments were quantified using imaging software and differential staining for plasmid (red) and cellular DNA (DAPI counterstaining (blue)). FIG. 5A shows no nuclear import. FIG. 5B shows intermediate nuclear import.

FIG. 5C shows total nuclear import. Thus, nuclear import can be observed and quantified using PNA-labeled plasmid DNA. PNA-labeled plasmids containing the SV40 DTS and lacking the SV40 DTS served as positive and negative controls, respectively.

EXAMPLE 5

Figure 6:
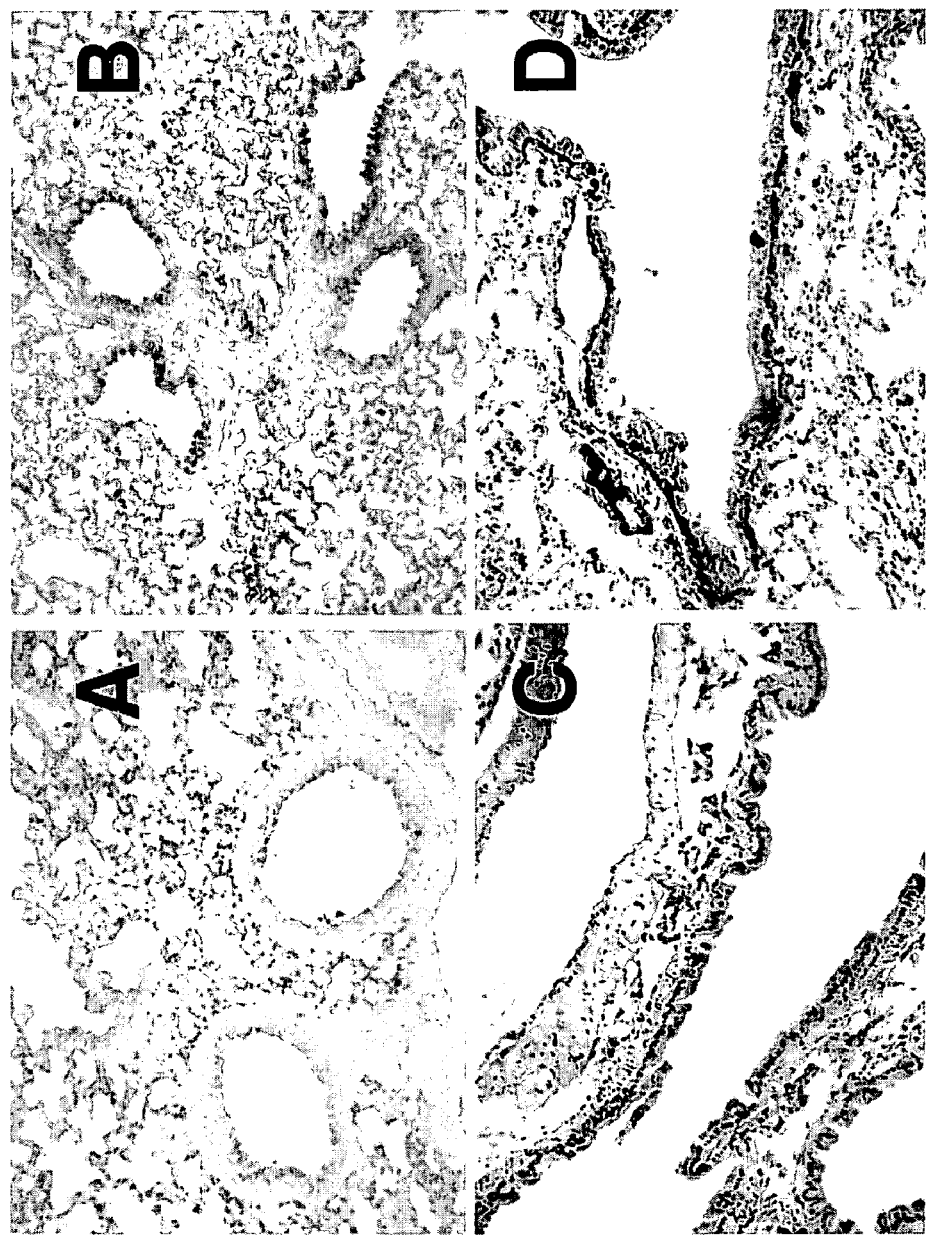
FIG. 6 shows transgene expression after plasmid delivery by endotracheal tube and electroporation using non-invasive surface electrodes for electroporation in vivo.

Human SP-C promoter (−318 to +46) nuclear targeting sequences and electroporation for safe and effective in vivo delivery of transgenes to the lung The sequence- and cell-specificity of the human SP-C promoter allows safe and effective in vivo delivery of transgenes in plasmids to pulmonary epithelia using endotracheal tube administration, and application electrodes placed on the chest. Following DNA delivery and electroporation as described (Dean et al., Gene Therapy 10:1608 [2003], herein incorporated by reference in its entirety), animals were allowed to recover, and gene expression was assessed one to three days later. Inclusion of the SV40 enhancer nuclear targeting sequence mediates gene expression in all cell types in the lung, including alveolar and airway epithelial cells, smooth muscle cells, and endothelial cells. (FIG. 6B). With 100 µg of DNA delivery by electroporation, very nearly 10 ng of gene product per gram wet weight of lung is obtained. No lung injury results from this procedure, and no increase in IL-6 levels are detected. Thus, endotracheal DNA delivery followed by electroporation is a safe and effective method for transgene expression in the lung. FIGS. 6C and 6D show use of the SMGA promoter fragment in place of the SV40 enhancer as a nuclear targeting sequence. FIG. 6C depicts luciferase gene expression from the plasmid carrying the SMGA DTS, showing that nuclear import in vivo can be restricted to smooth muscle cells in the lung. FIG. 6D depicts immunohistochemical staining of the marker smooth muscle alpha actin, showing the location of smooth muscle in the section, and that luciferase expression in FIG. 6c is in fact confined to smooth muscle cells. Thus, using specific nuclear targeting sequences it is possible to safely and effectively promote gene expression in a restricted and cell-specific fashion in the lung.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention that are obvious to those skilled in the relevant fields are intended to be within the scope of the following claims.

I claim:

1. A method for tissue specific nuclear import, comprising:
   a) providing
      i) a construct comprising a cell-specific nuclear targeting signal operably linked to a nucleic acid of interest, wherein said cell-specific nuclear targeting signal comprises at least nucleotides 149 to 337 of the surfactant protein C(SPC) promoter region; shown in SEQ ID NO:1 that functions as a nuclear targeting signal; and
      ii) a non-dividing mouse or human alveolar type II cell in vitro; and
   b) contacting said cell with said construct under conditions such that said nucleic acid of interest is expressed in the nucleus of said cell.

2. The method of claim 1, wherein said construct is within a vector selected from the group comprising a plasmid vector and a viral vector.

3. The method of claim 1, wherein said lung cell-specific nuclear targeting signal comprises SEQ ID NO: 1.

4. The method of claim 1, wherein said lung cell-specific nuclear targeting signal comprises nucleotides 149-365 of SEQ ID NO. 1.

5. The method of claim 1, wherein said lung cell-specific nuclear targeting signal comprises nucleotides 1 to 337 of SEQ ID NO. 1.

* * * * *

UNITED STATES PATENT AND TRADEMARK OFFICE
CERTIFICATE OF CORRECTION

PATENT NO. : 7,604,798 B2
APPLICATION NO. : 11/182933
DATED : October 20, 2009
INVENTOR(S) : Dean It is certified that error appears in the above-identified patent and that said Letters Patent is hereby corrected as shown below:

Column 1, line 10, the Federal Funding should read -- The government has certain rights in the invention. --

Column 20, line 41-54 should read
-- 1. A method for tissue specific nuclear import, comprising:
   a) providing
      i) a construct comprising a lung cell-specific nuclear targeting signal operably linked to a nucleic acid of interest, wherein said lung cell-specific nuclear targeting signal comprises at least nucleotides 149 to 337 of the surfactant protein C (SPC) promoter region shown in SEQ ID NO:1 that functions as a nuclear targeting signal; and
      ii) a non-dividing mouse or human alveolar type II cell in vitro; and
   b) contacting said cell with said construct under conditions such that said nucleic acid of interest is expressed in the nucleus of said cell. --

Signed and Sealed this

Twenty-seventh Day of April, 2010

David J. Kappos
*Director of the United States Patent and Trademark Office*

```
                          SEQUENCE LISTING

<160> NUMBER OF SEQ ID NOS: 1

<210> SEQ ID NO 1
<211> LENGTH: 365
<212> TYPE: DNA
<213> ORGANISM: Homo sapiens

<400> SEQUENCE: 1
ggcagcaggg gcaggtgcca gcaaggaagg caggcacgcc aggaagacac ccatggtgag      60
aagtgcagat ggcccgaggg caagtttgct caactcaccc aggtttgctc ttgctggggc     120
caagaggact catgtgccag ggccaagggc ccttgggggc tctcacaggg ggcttatctg     180
ggcttcggtt ctggagggcc aggaacaaac aggcttcaaa gccaagggct tggctggcac     240
acagggggct tggtccttca cctctgtccc ctctccctac ggacacatat aagaccctgg     300
tcacacctgg gagaggagga gaggagagca tagcacctgc agcaagatgg atgtgggcag     360
caaag                                                                 365
```